(12) United States Patent
Vaillant (10) Patent No.: US 9,603,865 B2
(45) Date of Patent: Mar. 28, 2017

(54) METHODS FOR THE TREATMENT OF HEPATITIS B AND HEPATITIS D VIRUS INFECTIONS

(71) Applicant: REPLICOR INC., Montreal (CA)

(72) Inventor: Andrew Vaillant, Roxboro (CA)

(73) Assignee: REPLICOR INC., Montreal QC (CA)

( * ) Notice: Subject to any disclaimer, the term of this patent is extended or adjusted under 35 U.S.C. 154(b) by 0 days.

(21) Appl. No.: 14/794,129

(22) Filed: Jul. 8, 2015

(65) Prior Publication Data

US 2016/0008393 A1     Jan. 14, 2016

Related U.S. Application Data

(60) Provisional application No. 62/022,846, filed on Jul. 10, 2014, provisional application No. 62/091,943, filed on Dec. 15, 2014.

(51) Int. Cl.

| | | |
|---|---|---|
| *A61K 48/00* | (2006.01) | |
| *C07H 21/02* | (2006.01) | |
| *C07H 21/04* | (2006.01) | |
| *A61K 31/7125* | (2006.01) | |
| *A61K 31/522* | (2006.01) | |
| *A61K 31/683* | (2006.01) | |
| *A61K 45/06* | (2006.01) | |
| *A61K 31/675* | (2006.01) | |
| *A61K 31/7088* | (2006.01) | |

(52) U.S. Cl.
CPC ........ *A61K 31/7125* (2013.01); *A61K 31/522* (2013.01); *A61K 31/675* (2013.01); *A61K 31/683* (2013.01); *A61K 31/7088* (2013.01); *A61K 45/06* (2013.01)

(58) Field of Classification Search
CPC .. A61K 48/00; A61K 2300/00; C12N 15/113; C12N 2310/11
See application file for complete search history.

(56) References Cited

U.S. PATENT DOCUMENTS

| | | | | |
|---|---|---|---|---|
| 5,482,836 A | * | 1/1996 | Cantor | ............... C12N 15/1003 204/456 |
| 8,008,269 B2 | | 8/2011 | Vaillant et al. | |
| 9,133,458 B2 | | 9/2015 | Bazinet et al. | |
| 2009/0317418 A1 | * | 12/2009 | Catanzaro | ............ C07K 14/005 424/188.1 |
| 2013/0217756 A1 | * | 8/2013 | Cancilla | ................ C12N 15/111 514/44 A |

FOREIGN PATENT DOCUMENTS

| | | |
|---|---|---|
| WO | 2012/075114 | 6/2012 |
| WO | 2013/170386 | 11/2013 |
| WO | 2014/032176 | 3/2014 |

OTHER PUBLICATIONS

Vaillant et al., 2006, Antimicrobial Agents and Chemotherapy, 50: 1393-1401.
Lee et al., 2008, Virology, 372: 107-117.
Guzman et al., 2007, Antiviral Therapy, 12: 1147-1156.
Bernstein et al., Antimicrobiol Agents and Chemotherapy, 2008, 52: 2727-2733.
Cardin et al., 2009, Virology Journal, 6: 1-14.
Matsumura et al., 2009, Gastroenterology, 137: 673-681.
Noordenn et al., 2013, Antimicrobial Agents and Chemotherapy, 57: 5291-5298.
Al Mahtab et al., 2011, Hepatology, AASLD Abstract #235, 478A-479A.
Al Mahtab et al., 2013, Journal of Hepatology, 58: S229-S407, Abstract # 776.
Geary et al., 2015, Advanced Drug Delivery Reviews, 87: 46-51.

* cited by examiner

*Primary Examiner* — Amy Bowman
(74) *Attorney, Agent, or Firm* — Norton Rose Fulbright Canada (57) ABSTRACT

It is disclosed a method for treating hepatitis B virus infection or hepatitis B virus/hepatitis delta virus co-infection, the method comprising administering to a subject in need of such treatment a first pharmaceutically acceptable agent that comprises at least one phosphorothioated nucleic acid polymer and a second pharmaceutically acceptable agent that comprises at least one nucleoside/nucleotide analog HBV polymerase inhibitor.

18 Claims, 5 Drawing Sheets

Fig. 1

*below cut-off for serum HBsAg detection in local ELISA (HBsAg negative)

SEQUENCE LISTING

```
<160> NUMBER OF SEQ ID NOS: 20

<210> SEQ ID NO 1
<211> LENGTH: 40
<212> TYPE: DNA
<213> ORGANISM: Artificial Sequence
<220> FEATURE:
<223> OTHER INFORMATION: fully phosphorothioated

<400> SEQUENCE: 1
cacacacaca cacacacaca cacacacaca cacacacaca                            40

<210> SEQ ID NO 2
<211> LENGTH: 40
<212> TYPE: DNA
<213> ORGANISM: Artificial Sequence
<220> FEATURE:
<223> OTHER INFORMATION: REP 2055, fully phosphorothioated

<400> SEQUENCE: 2
acacacacac acacacacac acacacacac acacacacac                            40

<210> SEQ ID NO 3
<211> LENGTH: 40
<212> TYPE: DNA
<213> ORGANISM: Artificial Sequence
<220> FEATURE:
<223> OTHER INFORMATION: REP 2148, fullly phosphorothioated, C = 5'
      methylcytidine

<400> SEQUENCE: 3
acacacacac acacacacac acacacacac acacacacac                            40

<210> SEQ ID NO 4
<211> LENGTH: 40
<212> TYPE: DNA
<213> ORGANISM: Artificial Sequence
<220> FEATURE:
<223> OTHER INFORMATION: fully phosphorothioated, C = 5' methylcytidine

<400> SEQUENCE: 4
cacacacaca cacacacaca cacacacaca cacacacaca                            40

<210> SEQ ID NO 5
<211> LENGTH: 40
<212> TYPE: RNA
<213> ORGANISM: Artificial Sequence
<220> FEATURE:
<223> OTHER INFORMATION: REP 2153, fully phosphorothioated, fully 2' O
```

-continued methylribose modified

<400> SEQUENCE: 5
acacacacac acacacacac acacacacac acacacacac                    40

<210> SEQ ID NO 6
<211> LENGTH: 40
<212> TYPE: RNA
<213> ORGANISM: Artificial Sequence
<220> FEATURE:
<223> OTHER INFORMATION: fully phosphorothioated, fully 2' O
      methylribose modified

<400> SEQUENCE: 6
cacacacaca cacacacaca cacacacaca cacacacaca                    40

<210> SEQ ID NO 7
<211> LENGTH: 40
<212> TYPE: DNA
<213> ORGANISM: Artificial Sequence
<220> FEATURE:
<223> OTHER INFORMATION: REP 2033, fully phosphorothioated

<400> SEQUENCE: 7
tgtgtgtgtg tgtgtgtgtg tgtgtgtgtg tgtgtgtgtg                    40

<210> SEQ ID NO 8
<211> LENGTH: 40
<212> TYPE: DNA
<213> ORGANISM: Artificial Sequence
<220> FEATURE:
<223> OTHER INFORMATION: fully phosphorothioated

<400> SEQUENCE: 8
gtgtgtgtgt gtgtgtgtgt gtgtgtgtgt gtgtgtgtgt                    40

<210> SEQ ID NO 9
<211> LENGTH: 40
<212> TYPE: RNA
<213> ORGANISM: Artificial Sequence
<220> FEATURE:
<223> OTHER INFORMATION: fully phosphorothioated, fully 2' O
      methylribose modifed, each cytosine 5' methylated

<400> SEQUENCE: 9
cacacacaca cacacacaca cacacacaca cacacacaca                    40

<210> SEQ ID NO 10
<211> LENGTH: 40
<212> TYPE: RNA
<213> ORGANISM: Artificial Sequence
<220> FEATURE:
<223> OTHER INFORMATION: REP 2139, fully phosphorothioated, fully 2' O
      methylribose modified, each cytosine 5' methylated

<400> SEQUENCE: 10
acacacacac acacacacac acacacacac acacacacac                    40

<210> SEQ ID NO 11
<211> LENGTH: 40
<212> TYPE: DNA
<213> ORGANISM: Artificial Sequence
<220> FEATURE:
<223> OTHER INFORMATION: REP 2163, fully phosphorothioated, each
      cytosine 5' methylated
<220> FEATURE:
<221> NAME/KEY: misc_feature

```
<222> LOCATION: 1,3,5,7,9,11,13,15,17,19,21,23,25,27,29,31,33,35,
      37,39
<223> OTHER INFORMATION: 2' O methylribose modification

<400> SEQUENCE: 11
acacacacac acacacacac acacacacac acacacacac                           40

<210> SEQ ID NO 12
<211> LENGTH: 40
<212> TYPE: RNA
<213> ORGANISM: Artificial Sequence
<220> FEATURE:
<223> OTHER INFORMATION: REP 2164, fully phosphorothioated, each
      cytosine 5' methylated
<220> FEATURE:
<221> NAME/KEY: misc_feature
<222> LOCATION: 1-12, 14-26, 28-40
<223> OTHER INFORMATION: 2' O methylribose modification

<400> SEQUENCE: 12
acacacacac acacacacac acacacacac acacacacac                           40

<210> SEQ ID NO 13
<211> LENGTH: 40
<212> TYPE: RNA
<213> ORGANISM: Artificial Sequence
<220> FEATURE:
<223> OTHER INFORMATION: REP 2165, fully phosphorothioated, each
      cytosine 5' methylated
<220> FEATURE:
<221> NAME/KEY: misc_feature
<222> LOCATION: 1-10, 12-20, 22-30, 32-40
<223> OTHER INFORMATION: 2' O methylribose modification

<400> SEQUENCE: 13
acacacacac acacacacac acacacacac acacacacac                           40

<210> SEQ ID NO 14
<211> LENGTH: 40
<212> TYPE: RNA
<213> ORGANISM: Artificial Sequence
<220> FEATURE:
<223> OTHER INFORMATION: REP 2166, full phosphorothioated, each cytosine
      5' methylated and 2'O methylribose modified

<400> SEQUENCE: 14
acacacacac acacacacac acacacacac acacacacac                           40

<210> SEQ ID NO 15
<211> LENGTH: 40
<212> TYPE: DNA
<213> ORGANISM: Artificial Sequence
<220> FEATURE:
<223> OTHER INFORMATION: REP 2167, fully phosphorothioated, each
      cytosine 5' methylated
<220> FEATURE:
<221> NAME/KEY: misc_feature
<222> LOCATION: 2,4,6,8,10,12,14,16,18,20,22,24,26,28,30,32,34
      36,38,40
<223> OTHER INFORMATION: 2' O methyribose modification

<400> SEQUENCE: 15
acacacacac acacacacac acacacacac acacacacac                           40

<210> SEQ ID NO 16
<211> LENGTH: 40
<212> TYPE: DNA
<213> ORGANISM: Artificial Sequence
<220> FEATURE:
```

```
<223> OTHER INFORMATION: fully phosphorothioated, each cytosine 5'
      methylated
<220> FEATURE:
<221> NAME/KEY: misc_feature
<222> LOCATION: 2,4,6,8,10,12,14,16,18,20,22,24,26,28,30,32,34
      36,38,40
<223> OTHER INFORMATION: 2' O methylribose modification

<400> SEQUENCE: 16
cacacacaca cacacacaca cacacacaca cacacacaca                              40

<210> SEQ ID NO 17
<211> LENGTH: 40
<212> TYPE: RNA
<213> ORGANISM: Artificial Sequence
<220> FEATURE:
<223> OTHER INFORMATION: fully phosphorothioated, each cytosine 5'
      methylated
<220> FEATURE:
<221> NAME/KEY: misc_feature
<222> LOCATION: 1-13, 15-27, 29-40
<223> OTHER INFORMATION: 2' O methylribose modification

<400> SEQUENCE: 17
cacacacaca cacacacaca cacacacaca cacacacaca                              40

<210> SEQ ID NO 18
<211> LENGTH: 40
<212> TYPE: RNA
<213> ORGANISM: Artificial Sequence
<220> FEATURE:
<223> OTHER INFORMATION: fully phosphorothioated, each cytosine 5'
      methylated
<220> FEATURE:
<221> NAME/KEY: misc_feature
<222> LOCATION: 1-9, 11-29, 21-29, 31-40
<223> OTHER INFORMATION: 2' O methylribose modification

<400> SEQUENCE: 18
cacacacaca cacacacaca cacacacaca cacacacaca                              40

<210> SEQ ID NO 19
<211> LENGTH: 40
<212> TYPE: RNA
<213> ORGANISM: Artificial Sequence
<220> FEATURE:
<223> OTHER INFORMATION: fully phosphorothioated, each cytosine
      5' methylated and 2'O methylribose modified

<400> SEQUENCE: 19
cacacacaca cacacacaca cacacacaca cacacacaca                              40

<210> SEQ ID NO 20
<211> LENGTH: 40
<212> TYPE: DNA
<213> ORGANISM: Artificial Sequence
<220> FEATURE:
<223> OTHER INFORMATION: fully phosphorothioated, each cytosine 5'
      methylated
<220> FEATURE:
<221> NAME/KEY: misc_feature
<222> LOCATION: 1,3,5,7,9,11,13,15,17,19,21,23,25,27,29,31,33,35,
      37,39
<223> OTHER INFORMATION: 2' O methylribose modification

<400> SEQUENCE: 20
cacacacaca cacacacaca cacacacaca cacacacaca                              40
```

METHODS FOR THE TREATMENT OF HEPATITIS B AND HEPATITIS D VIRUS INFECTIONS

TECHNICAL FIELD

The present description relates to methods of treating a subject with hepatitis B virus (HBV) infection or HBV/hepatitis delta virus (HDV) co-infection comprising administering a first pharmaceutically acceptable phosphorothioated nucleic acid polymer formulation and a second pharmaceutically acceptable nucleoside/nucleotide analog formulation that inhibits the HBV polymerase.

BACKGROUND ART

HBV afflicts 400 million individuals worldwide and causes an estimated 600,000 deaths each year from complications arising from HBV infection. While several antiviral treatments are approved for use, none of these is able to elicit a therapeutically effective immune response capable of providing durable control of infection except in a small fraction of patients undergoing treatment.

HBV infection results in the production of two different particles: 1) the infectious HBV virus itself (or Dane particle) which includes a viral capsid assembled from the HBV core antigen protein (HBcAg) and is covered by the HBV surface antigen (HBsAg) and 2) subviral particles (or SVPs) which are high density lipoprotein-like particles comprised of lipids, cholesterol, cholesterol esters and the small and medium forms of the HBV surface antigen (HBsAg) which are non-infectious. For each viral particle produced, 1,000-10,000 SVPs are released into the blood. As such SVPs (and the HBsAg protein they carry) represent the overwhelming majority of viral protein in the blood. HBV infected cells also secrete a soluble proteolytic product of the pre-core protein called the HBV e-antigen (HBeAg).

HDV uses HBsAg to form its viral structure (Taylor, 2006, Virology, 344: 71-76) and as such, HDV infection can only occur in subjects with concomitant HBV infection. While the incidence of HDV co-infection in asymptomatic HBV carriers and chronic HBV-related liver disease is low in countries with a low incidence of HBV infection, it is a significant complication in HBV-infected subjects in countries with a high incidence of HBV infection and can increase the rate of progression of liver disease to liver cirrhosis. The unmet medical need in HBV infection is even more pressing in HBV/HDV co-infected subjects; there is no specific approved agent that directly targets the HDV virus and patient response even to combination therapy with approved agents for HBV treatment is poorer than patients in with HBV monoinfection (Wedemeyer et al., 2014, Oral abstract 4, 49$^{th}$ Annual Meeting of the European Association for the Study of the Liver, April 9-14, London, UK).

The current approved treatments for HBV include interferon-α or thymosin α1-based immunotherapies and the suppression of viral production by inhibition of the HBV polymerase by nucleoside/nucleotide analogs. HBV polymerase inhibitors are effective in reducing the production of infectious virions but have little to no effect in reducing HBsAg or only very slowly reduce HBsAg with long term treatment in a limited number of patients (Fung et al., 2011, Am. J. Gasteroenterol., 106: 1766-1773; Reijnders et al., 2011, J. Hepatol., 54: 449-454; Charuworn et al., 2014, Poster abstract 401, 48$^{th}$ Annual Meeting of the European Association for the Study of the Liver, April 24-28, Amsterdam, The Netherlands). The primary effect of HBV polymerase inhibitors is to block the transformation of pre-genomic viral mRNA into partially double stranded DNA, which is present in infectious virions. Interferon based immunotherapy can achieve a reduction of infectious virus and removal of HBsAg from the blood but only in a small percentage of treated subjects.

HBsAg in the blood can sequester anti-HBsAg antibodies and allow infectious viral particles to escape immune detection which is likely one of the reasons why HBV infection remains a chronic condition. In addition HBsAg, HBeAg and HBcAg all have immuno-inhibitory properties as discussed below and the persistence of these viral proteins in the blood of patients following the administration of any of the currently available treatments for HBV as described above likely has a significant impact in preventing patients from achieving immunological control of their HBV infection.

Although the three primary HBV proteins (HBsAg, HBeAg and HBcAg) all have immuno-inhibitory properties (see below), HBsAg comprises the overwhelming majority of HBV protein in the circulation of HBV infected subjects and is likely the primary mediator of inhibition of the host immune response to HBV infection. While the removal of HBeAg, appearance of anti-HBe or reductions in serum viremia are not correlated with the development of sustained control of HBV infection off treatment, the removal of serum HBsAg from the blood (and appearance of free anti-HBsAg antibodies) in HBV infection is a well-recognized excellent prognostic indicator of antiviral response on treatment which will lead to control of HBV infection off treatment (although this only occurs in a small fraction of patients receiving immunotherapy or HBV polymerase inhibitors). Thus, while reduction of all three major HBV proteins (HBsAg, HBeAg and HBcAg) may result in the optimal removal of inhibitory effect, the removal of HBsAg is essential and its removal alone is likely sufficient to remove the bulk of the inhibition of immune function in subjects with HBV infection.

Another critical feature of chronic HBV infection is the establishment of a stable reservoir of HBV genetic information in the nucleus of infected cells called covalently closed circular DNA (cccDNA). cccDNA exists in multiple copies within the nucleus as an extrachromosomal episome which functions as the transcriptional template for the production of mRNA encoding all viral proteins and immature genomes (pre-genomic mRNA) for the production of new virions. After encapsidation in the cytoplasm, the immature pre-genomic mRNA is converted into a mature, partially double stranded DNA genome by the HBV polymerase (which is co-encapsidated with the pregenomic mRNA), thereby rendering the mature HBV genome competent to establish or replenish a cccDNA reservoir in naïve or previously infected cells. The end of the infectious process consists of the delivery of this partially double stranded genomic HBV template into the nucleus and its conversion to cccDNA.

cccDNA can be replenished in the nucleus of infected cells via nuclear import of HBV capsids containing mature HBV genomes which replenish the cccDNA copy number. This nuclear cccDNA replenishment is accomplished by two mechanisms: direct nuclear import of assembled capsids from the cytoplasm or re-infection of previously infected hepatocytes with subsequent shuttling of the internalized capsids into the nucleus (Rabe et al., 2003, Proc. Natl. Acad. Sci. USA, 100: 9849-9854). The transcriptional inhibition or elimination of this genomic HBV reservoir in the nucleus is critical to the establishment of long term control of HBV infection following treatment.

Long term treatment with nucleoside/nucleotide HBV polymerase inhibitors can reduce cccDNA copy number within the nucleus, consistent with the ability of HBV polymerase inhibitors to block replenishment of cccDNA by nuclear import of capsids containing mature HBV genomes. However, while the cccDNA copy number per hepatocyte is reduced, it still remains transcriptionally active thus HBsAg levels remain largely unaffected (Werle-Lapostolle et al., 2004, Gastroenterol., 126: 1750-1758; Wong et al., 2013, Clin. Gastroenterol. Hepatol., 11: 1004-1010; Wong et al., 2014, Poster abstract 1074, 49$^{th}$ Annual Meeting of the European Association for the Study of the Liver, April 9-14, London, UK). cccDNA can be transcriptionally inactivated by immune-mediated processes (Belloni et al., 2012, J. Clin. Inv., 122: 529-537) but the ability of the immune response to provoke cytokine responses required for cccDNA inactivation is likely blocked by persistently circulating HBsAg as described in U.S. 2014/0065102 (which is incorporated herein by reference in its entirety) and is consistent with the ineffectiveness of immunotherapies in treating HBV infection.

As such, there exists a clear unmet medical need for a treatment regimen which can elicit a durable immunological control of HBV infection in a large proportion of patients receiving this treatment.

SUMMARY

In accordance with the present description there is now provided a method for the treatment of HBV infection or HBV/HDV co-infection in a subject requiring such treatment, the method comprising the administration of a first pharmaceutically acceptable agent which comprises at least one phosphorothioated nucleic acid polymer and a second pharmaceutically acceptable agent which comprises at least one nucleoside/nucleotide analog HBV polymerase inhibitor.

It is also provided a composition comprising a first pharmaceutically acceptable agent which comprises at least one phosphorothioated nucleic acid polymer and a second pharmaceutically acceptable agent which comprises at least one nucleoside/nucleotide analog HBV polymerase inhibitor for treating HBV infection or HBV/HDV co-infection in a subject.

It is also provided a composition comprising a first pharmaceutically acceptable agent which comprises a chelate complex of at least one phosphorothioated nucleic acid polymer and a second pharmaceutically acceptable agent which comprises at least one nucleoside/nucleotide analog HBV polymerase inhibitor for treating HBV infection or HBV/HDV co-infection in a subject.

In an embodiment, it is provided a method of treating HBV infection or HBV/HDV co-infection in a subject comprising administering a first pharmaceutically acceptable agent which comprises a chelate complex of one or more nucleic acid polymers selected from the following:
SEQ ID NO: 2;
SEQ ID NO: 10;
SEQ ID NO 13;
SEQ ID NOs: 1, 3-9, 11, 12 and 14-20;
a phosphorothioated oligonucleotide from 20-120 nucleotides in length comprising repeats of the sequence AC;
a phosphorothioated oligonucleotide from 20-120 nucleotides in length comprising repeats of the sequence CA;
a phosphorothioated oligonucleotide from 20-120 nucleotides in length comprising repeats of the sequence TG and
a phosphorothioated oligonucleotide from 20-120 nucleotides in length comprising repeats of the sequence GT;
and a second pharmaceutically acceptable agent which comprises one or more of the following:
lamivudine;
adefovir dipivoxil;
entecavir;
telbivudine;
tenofovir disoproxil fumarate;
entricitabine;
clevudine;
besifovir;
tenofovir alafenamide fumarate;
AGX-1009;
elvucitabine;
lagociclovir valactate;
pradefovir mesylate;
valtorcitabine; and
any nucleoside/nucleotide analog which inhibits the HBV polymerase.

In another embodiment, it is provided a composition comprising a first pharmaceutically acceptable agent which comprises a chelate complex of one or more nucleic acid polymers selected from the following:
SEQ ID NO: 2;
SEQ ID NO: 10;
SEQ ID NO 13;
SEQ ID NOs: 1, 3-9, 11, 12 and 14-20;
a phosphorothioated oligonucleotide from 20-120 nucleotides in length comprising repeats of the sequence AC;
a phosphorothioated oligonucleotide from 20-120 nucleotides in length comprising repeats of the sequence CA;
a phosphorothioated oligonucleotide from 20-120 nucleotides in length comprising repeats of the sequence TG and
a phosphorothioated oligonucleotide from 20-120 nucleotides in length comprising repeats of the sequence GT;
and a second pharmaceutically acceptable agent which comprises one or more of the following:
lamivudine;
adefovir dipivoxil;
entecavir;
telbivudine;
tenofovir disoproxil fumarate;
entricitabine;
clevudine;
besifovir;
tenofovir alafenamide fumarate;
AGX-1009;
elvucitabine;
lagociclovir valactate;
pradefovir mesylate;
valtorcitabine; and
any nucleoside/nucleotide analog which inhibits the HBV polymerase
for the treatment of HBV infection or HBV/HDV co-infection.

In another embodiment, the nucleic acid polymer comprises a phosphorothioated oligonucleotide from 20-120 nucleotides in length comprising repeats of the sequence AC.

In another embodiment, the nucleic acid polymer comprises a phosphorothioated oligonucleotide from 20-120 nucleotides in length comprising the repeats of the sequence CA.

In another embodiment, the nucleic acid polymer comprises a phosphorothioated oligonucleotide from 20-120 nucleotides in length comprising the repeats of the sequence TG.

In another embodiment, the nucleic acid polymer comprises a phosphorothioated oligonucleotide from 20-120 nucleotides in length comprising the repeats of the sequence GT.

In another embodiment, the phosphorothioated nucleic acid polymer further comprises at least one 2' ribose modification.

In another embodiment, the phosphorothioated nucleic acid polymer further comprises all riboses having a 2' modification.

In another embodiment, the phosphorothioated nucleic acid polymer further comprises at least one 2' O methyl ribose modification.

In another embodiment, the phosphorothioated nucleic acid polymer further comprises all riboses having the 2' O methyl modification.

In another embodiment, the phosphorothioated nucleic acid polymer further comprises at least one 5' methylcytosine.

In another embodiment, the phosphorothioated nucleic acid polymer further comprises all cytosines present as 5' methylcytosine.

In another embodiment, the phosphorothioated nucleic acid polymer further comprises at least one 2' ribose modification and at least one 5' methylcytosine.

In another embodiment, the phosphorothioated nucleic acid polymer further comprises all riboses having the 2' O methyl modification and all cytosines present as 5' methylcytosine.

In another embodiment, the nucleic acid polymer is selected from the group consisting of SEQ ID NOs: 1-20.

In another embodiment, the nucleic acid polymer is prepared as an oligonucleotide chelate complex comprising an oligonucleotide selected from the group consisting of SEQ ID NOs: 1-20.

In another embodiment, the nucleic acid polymer is an oligonucleotide consisting of SEQ ID NO: 2.

In another embodiment, the nucleic acid polymer is prepared as an oligonucleotide chelate complex comprising SEQ ID NO: 2.

In another embodiment, the nucleic acid polymer is an oligonucleotide consisting of SEQ ID NO: 10.

In another embodiment, the nucleic acid polymer is prepared as an oligonucleotide chelate complex comprising SEQ ID NO: 10.

In another embodiment, the nucleic acid polymer is an oligonucleotide consisting of SEQ ID NO: 13.

In another embodiment, the nucleic acid polymer is prepared as an oligonucleotide chelate complex comprising SEQ ID NO: 13.

In an embodiment, the chelate complex is a calcium chelate complex.

In another embodiment, the chelate complex is a magnesium chelate complex.

In an additional embodiment, the chelate complex is a calcium/magnesium chelate complex.

In a further embodiment, the first and second pharmaceutically acceptable agents are formulated within the same pharmaceutical composition.

In a further embodiment, the first and second agents are formulated within separate pharmaceutical compositions.

In a further embodiment, the first and second agents are formulated for a simultaneous administration.

In a further embodiment, the first and second agents are formulated for an administration by a different route.

In a further embodiment, the first and second agents are formulated for an administration using one or more of the following: oral ingestion, aerosol inhalation, subcutaneous injection, intravenous injection and intravenous infusion.

In a further embodiment, the nucleic acid polymer is at least one of:
  SEQ ID NO: 2;
  SEQ ID NO: 10;
  SEQ ID NO: 13;
  SEQ ID NOs: 1, 3-9, 11, 12 and 14-20;
  a phosphorothioated oligonucleotide from 20-120 nucleotides in length comprising repeats of the sequence AC;
  a phosphorothioated oligonucleotide from 20-120 nucleotides in length comprising repeats of the sequence CA;
  a phosphorothioated oligonucleotide from 20-120 nucleotides in length comprising repeats of the sequence TG and
  a phosphorothioated oligonucleotide from 20-120 nucleotides in length comprising repeats of the sequence GT.

In a further embodiment, the following nucleic acid polymers can be further formulated as an oligonucleotide chelate complex:
  SEQ ID NO: 2;
  SEQ ID NO: 10;
  SEQ ID NO 13;
  SEQ ID NOs: 1, 3-9, 11, 12 and 14-20;
  a phosphorothioated oligonucleotide from 20-120 nucleotides in length comprising repeats of the sequence AC;
  a phosphorothioated oligonucleotide from 20-120 nucleotides in length comprising repeats of the sequence CA;
  a phosphorothioated oligonucleotide from 20-120 nucleotides in length comprising repeats of the sequence TG; and
  a phosphorothioated oligonucleotide from 20-120 nucleotides in length comprising repeats of the sequence GT.

In another embodiment, the nucleoside/nucleotide analog HBV polymerase inhibitor comprises one or more of the following:
  lamivudine;
  adefovir dipivoxil;
  entecavir;
  telbivudine;
  tenofovir disoproxil fumarate;
  entricitabine;
  clevudine;
  besifovir;
  tenofovir alafenamide fumarate;
  AGX-1009;
  elvucitabine;
  lagociclovir valactate;
  pradefovir mesylate;
  valtorcitabine; and
  any nucleoside/nucleotide analog which inhibits the HBV polymerase.

DETAILED DESCRIPTION

It is provided herein a combination therapy against HBV infection which consists of administering a first pharmaceutically acceptable agent capable of removing HBsAg from the blood and a second pharmaceutically acceptable agent which inhibits the HBV polymerase. Such a combination treatment allows recovery of host immune function (by removal of serum HBsAg) which in turn leads to the immune-mediated transcriptional inactivation of cccDNA and or reduction of cccDNA copy number in infected hepatocytes while simultaneously blocking replenishment of cccDNA via nuclear import of capsids containing mature HBV genomes or the production of infectious virus (by inhibiting the HBV polymerase). The combined synergistic effects of these two agents can accelerate the antiviral response to therapy and or the elimination of cccDNA from infected cells, thus shortening the time of therapy required to obtain sustained suppression of infection off treatment.

Importantly, these effects can be achieved in the absence of immunotherapy. This combination treatment will be effective in HBV monoinfection and HBV/HDV co-infection.

HBsAg plays a key role in HBV infection and HBV/HDV co-infection. Aside from its role as an essential structural component for virion formation, HBsAg is also released in large amounts into the blood of infected subjects in the form of subviral particles (SVPs), which lack the viral capsid and genome and which appear to function primarily to deliver HBsAg into the blood. SVPs are secreted from infected cells in 1,000-10,000 fold excess over virus secretion which allows SVPs to effectively sequester HBsAg antibodies (anti-HBs) so that HBV or HDV virus in the blood can escape recognition by adaptive immunity. Several studies have also suggested that HBsAg may also function to directly block activation of adaptive and innate immune responses to HBV infection (Cheng et al., 2005, Journal of hepatology, 43:4 65-471; Op den Brouw et al., 2009, Immunology, 126: 280-289; Vanlandschoot et al., 2002, The Journal of general virology, 83: 1281-1289; Wu et al., 2009, Hepatology, 49: 1132-1140; Xu et al., 2009, Molecular immunology, 46: 2640-2646). The presence of this functionality in human HBV infection and its impact on the activity of immunotherapeutic agents and the additional applicability of these antiviral effects in HBV/HDV co-infection has been previously described in US 2014/0065102 A1, which is incorporated herein by reference in its entirety. Although HBeAg and HBcAg have also been shown to have immuno-inhibitory properties (Kanda et al., 2012, J. Inf. Dis., 206: 415-420; Lang et al., 2011, J. Hepatol., 55: 762-769; Gruffaz et al., 2013, J. Hepatol., 58 (suppl), p s155, Abstract 378), these are likely of minimal impact given the very small proportion of HBeAg and HBcAg in relation to HBsAg in the blood.

Nucleoside/nucleotide analog inhibitors of HBV polymerase (NRTI's) are a well-known class of antiviral agents whose activity against HBV infection occurs by the same mechanism of action: this class of compounds act as immediate or delayed chain terminators by competing with natural nucleotide substrates during elongation of the DNA chain (Menendez-Arias et al., 2015 Curr. Op. Virol. 8: 1-9). This class of compounds can retain the fundamental core nucleotide/nucleoside core structure consisting of a nitrogenous base and sugar or can be acyclic nucleotides or can lack the sugar or pseudo sugar ring or can have a phosphonate group replacing the α-phosphate and can have many other additional modifications present as described in Michailidis et al., 2012 Int. J. Biochem. Cell. Biol. 44: 1060-1071 and De Clercq et al., 2010 Viruses 2: 1279-1305.

Duck HBV virus (DHBV)-infected ducks are an accepted model of HBV infection and have been used in the evaluation of several HBV NRTIs currently used to treat human patients (Schultz et al., 2004, Adv Virus Res, 63:1-70; Foster et al., 2005, J Virol, 79:5819-5832; Nicoll et al., 1998, Antimicrob Agents Chemother., 42:3130-3135). Nucleic acid polymers (NAPs) that are phosphorothioated have been shown to have antiviral activity in DHBV infected ducks (Noordeen et al., 2013 Anti-Microb. Agents Chemother. 57: 5291-5298 and 5299-5306) which is not derived from any direct immunostimulatory mechanisms. Moreover, therapeutic intervention with the NAP REP 2055 (SEQ ID NO:2) in previously established DHBV infection in vivo, REP 2055 led to the clearance of serum duck HBsAg (DHBsAg) which was accompanied by transcriptional inactivation of cccDNA and reduction in cccDNA copy number (Noordeen et al., 2009, Abstract 88 HEPDART meeting December 6-9, HI, USA). This inactivation and elimination of cccDNA is caused by removal of DHBsAg-mediated repression of the host immune function, which can then inactivate and clear cccDNA from infected cells by recognized, immune-mediated mechanisms (Levrero et al., 2009, J. Hepatol., 51: 581-592; Belloni et al., 2012, J. Clin. Inv., 122: 529-537).

NAPs effectively remove HBsAg from the blood of human patients as described in US 2014/0065102. In an accepted preclinical model of HBV infection (duck HBV infected Pekin ducks), NAP treatment resulted in the elimination of serum duck HBsAg (DHBsAg) and the restoration of immune function in the absence of serum DHBsAg was able to both transcriptionally inactivate and eliminate cccDNA from infected hepatocytes (Noordeen et al., 2009, Abstract 88, HEPDART meeting December 6-10, HI, USA). Thus, removal of HBsAg from the serum of HBV infected patients is expected to have the same effect on cccDNA inactivation in infected human hepatocytes in situ.

Therefore, it is described herein an effective means for more rapidly establishing control of serum viremia or for establishing durable control of cccDNA activity and or its elimination from HBV infected hepatocytes which consists of a novel combined approach whereby HBsAg is reduced or eliminated from the blood by the use of a pharmaceutically acceptable phosphorothioated NAP formulation and replenishment of cccDNA and production of infectious virus is blocked by a second pharmaceutically acceptable nucleotide/nucleoside analog formulation inhibiting the HBV polymerase. This combined approach has the following novel and important benefits:

1) it combines the ability of an improved host immune function (caused by removal of serum HBsAg) to transcriptionally inactivate and or reduce cccDNA copy number within the cell with the blockade of cccDNA replenishment (by preventing capsids containing mature genomes from entering the nucleus (by inhibition of HBV polymerase activity) or production of infectious virions (my preventing the transformation of pregenomic RNA into partially double stranded DNA within the HBV capsid;
2) it has a synergistic effect on reducing the duration of treatment required to remove, eliminate or establish transcriptional suppression of cccDNA or control of serum viremia from infected hepatocytes in the liver because of the overlapping effects of said two pharmaceutically acceptable agents; and
3) it does not require the use of an immunotherapy (as taught to be specifically required in U.S. 2014/0065102) to achieve sustained control of HBV infection after treatment which would be an important therapeutic improvement, given the poor tolerability of immunotherapy in many patients.

The improved antiviral effects with methods described above will have the same therapeutic benefit in patients with HBV mono-infection and HBV/HDV co-infection as HDV infection cannot exist in the absence of HBV infection as described above.

Therefore, in the absence of any current treatment regimen which can either eliminate or establish durable control of cccDNA activity without the use of immunotherapy in a large proportion of patients, it is provided herein for the first time an effective combination treatment against HBV infection and HBV/HDV co-infection which simultaneously reduces or clears HBsAg from the blood and which blocks cccDNA replenishment in the nucleus of HBV infected cells. These effects can be achieved by the use of a pharmaceutically acceptable phosphorothioated NAP formulation used in combination with a pharmaceutically acceptable nucleoside/nucleotide analog HBV polymerase inhibitor.

This novel combination approach is effective in the absence of immunotherapy, which has the important advantages of improving the tolerability of treatment and reducing the incidence of hematological and other side effects known to occur with immunotherapy.

The term oligonucleotide (ON) refers to an oligomer or polymer of ribonucleic acid (RNA) and/or deoxyribonucleic acid (DNA). This term includes ONs composed of modified nucleobases (including 5' methylcytosine and 4' thiouracil), sugars and covalent internucleoside (backbone) linkages as well as ONs having non-naturally-occurring portions which function similarly. Such modified or substituted ONs may be preferable over native forms because of desirable properties such as, for example, reduced immunoreactivity, enhanced cellular uptake, enhanced affinity for the nucleic acid target (in the context of antisense ONs, siRNAs and shRNAs) and/or increased stability to nuclease-mediated degradation. ONs can also be double stranded. ONs also include single stranded molecules such as antisense oligonucleotides, Speigelmers and aptamers and miRNAs, as well as double stranded molecules such as small interfering RNAs (siRNAs) or small hairpin RNAs (shRNAs).

ONs can include various modifications, e.g., stabilizing modifications, and thus can include at least one modification in the phosphodiester linkage and/or on the sugar, and/or on the base. For example, the ON can include, without restriction, one or more modifications, or be fully modified so as to contain all linkages or sugars or bases with the recited modifications. Modified linkages can include phosphorothioate linkages and phosphorodithioate linkages. While modified linkages are useful, the ONs can include phosphodiester linkages. Additional useful modifications include, without restriction, modifications at the 2'-position of the sugar including 2'-O-alkyl modifications such as 2'-O-methyl modifications, 2' O-methoxyethyl (2' MOE), 2'-amino modifications, 2'-halo modifications such as 2'-fluoro; acyclic nucleotide analogs. Other 2' modifications are also known in the art and can be used such as locked nucleic acids. In particular, the ON has modified linkages throughout or has every linkage modified, e.g., phosphorothioate; has a 3'- and/or 5'-cap; includes a terminal 3'-5' linkage; the ON is or includes a concatemer consisting of two or more ON sequences joined by a linker(s). Base modifications can include 5' methylation of the cytosine base (5' methylcytosine or in the context of a nucleotide, 5' methylcytidine) and/or 4' thioation of the uracil base (4' thiouracil or in the context of a nucleotide, 4' thiouridine). Different chemically compatible modified linkages can be combined where the synthesis conditions are chemically compatible such as having an oligonucleotide with phosphorothioate linkages, a 2' ribose modification (such as 2'O-methylation) and a modified base (such as 5' methylcytosine). The ON can further be completely modified with all of these different modifications (e.g. each linkage phosphorothioated, each ribose 2' modified and each base being modified).

As encompassed herein, the term "nucleic acid polymer" or NAP is any single stranded ON which contains no sequence specific functionality, either to hybridize with a nucleic acid target or adopt a sequence specific secondary structure which results in binding to a specific protein. The biochemical activity of NAPs are not dependent on Toll-like receptor recognition of ONs, hybridization with a target nucleic acid or aptameric interaction requiring a specific secondary/tertiary ON structure derived from a specific order of nucleotides present. NAPs can include base and or linkage and or sugar modifications as described above. NAPs require phosphorothioation to have antiviral activity. Exemplary antiviral NAP compounds are listed in Table 1:

TABLE 1

Examples of antiviral NAPs which can be useful in the current disclosure.

| Nucleic acid type | Sequence (5'-3') | Modifications |
|---|---|---|
| DNA | (dAdC)$_{20}$ (SEQ ID NO: 2) | All linkages PS |
| DNA | (dCdA)$_{20}$ (SEQ ID NO: 1) | All linkages PS |
| DNA | (dA-5'MedC)$_{20}$ (SEQ ID NO: 3) | All linkages PS |
| DNA | (5'MedC-dA)$_{20}$ (SEQ ID NO: 4) | All linkages PS |
| RNA | (AC)$_{20}$ (SEQ ID NO: 5) | All linkages PS; All riboses with 2'OMe modification |
| RNA | (CA)$_{20}$ (SEQ ID NO: 6) | All linkages PS; All riboses with 2'OMe modification |
| DNA | (dTdG)$_{20}$ (SEQ ID NO: 7) | All linkages PS |
| DNA | (dGdT)$_{20}$ (SEQ ID NO: 8) | All linkages PS |
| RNA | (5'MeC-A)$_{20}$ (SEQ ID NO: 9) | All linkages PS; All riboses with 2'OMe modification |
| RNA | (A-5'MeC)$_{20}$ (SEQ ID NO: 10) | All linkages PS; All riboses with 2'OMe modification |
| RNA/DNA | (A-5'MedC)$_{20}$ (SEQ ID NO: 11) | All linkages PS; All riboses on riboadenosine are 2'OMe modified |
| RNA | (A-5'MeC)$_{20}$ (SEQ ID NO: 12) | All linkages PS; All riboses with 2'OMe modification except riboadenosines at positions 13 and 27 (which are 2'H) |
| RNA | (A-5'MeC)$_{20}$ (SEQ ID NO: 13) | All linkages PS; All riboses with 2'OMe modification except riboadenosines at positions 11, 21 and 31 (which are 2'H) |
| RNA | (A-5'MeC)$_{20}$ (SEQ ID NO: 14) | All linkages PS; All 5'MeC riboses are 2'OMe modified |
| RNA/DNA | (dA-5'MeC)$_{20}$ (SEQ ID NO: 15) | All linkages PS; All 5'MeC riboses are 2'OMe modified |
| RNA/DNA | (5'MedC-A)$_{20}$ (SEQ ID NO: 16) | All linkages PS; All A riboses are 2'OMe modified |
| RNA | (5'MeC-A)$_{20}$ (SEQ ID NO: 17) | All linkages PS; All riboses with 2'OMe modification except riboadenosines at positions 14 and 28 (which are 2'H) |
| RNA | (5'MeC-A)$_{20}$ (SEQ ID NO: 18) | All linkages PS; All riboses with 2'OMe modification except riboadenosines at positions 10, 20 and 30 (which are 2'H) |
| RNA | (5'MeC-A)$_{20}$ (SEQ ID NO: 19) | All linkages PS; All 5'MeC riboses are 2'OMe modified |
| RNA/DNA | (5'MeC-dA)$_{20}$ (SEQ ID NO: 20) | All linkages PS; All 5'MeC riboses are 2'OMe modified | dA = deoxyadenosine,
A = adenosine,
dC = deoxycytidine,
C = cytidine,
dT = deoxythymidine,
dG = deoxyguanosine,
PS = phosphorothioate,
2'OMe = 2'O methyl,
5'MeC = 5'methylcytosine-modified cytidine,
5'MedC = 5'methylcytosine-modified deoxycytidine In the present disclosure, the term "ON chelate complex" refers to two or more ONs linked intermolecularly by a divalent or multivalent metal cation and can occur with single or double stranded ONs. ON chelate complexes neutralize the inherent chelation properties of ONs which can contribute to administration-related side effects with these compounds. The administration of ON chelate complexes is a method of administering an ON to a subject where administration-related side effects associated with un-chelated ONs (which are ONs administered as sodium salts as is commonly used in the art) are mitigated as described in U.S. Pat. Nos. 8,513,211 and 8,716,259, which are incorporated herein by reference in their entirety. These side effects may include shivering, fever and chills with intravenous infusion or induration, inflammation and pain at the injection site with subcutaneous administration. The administration of ON chelate complexes does not interfere with the biochemical activity of ONs when used normally as sodium salts. Thus any NAP described herein can be optionally prepared as an ON chelate complex without affecting its biochemical activity.

ON chelate complexes may contain diverse multivalent metal cations including calcium, magnesium, cobalt, iron, manganese, barium, nickel, copper, zinc, cadmium, mercury and lead. It is further demonstrated that chelation of these multivalent metal cations results in the formation of ON chelate complexes comprised of two or more ONs linked via metal cations and occur with ONs greater than 6 nucleotides in length, and in the presence of ONs with either phosphodiester or phosphorothioate linkages. ONs can optionally have each linkage phosphorothioated. Chelation also occurs with ONs containing 2' modifications (such as 2' O methyl) at the ribose or containing modified bases such as 5' methylcytosine or 4-thiouracil. These 2' modifications can be present on one or more or all riboses and modified bases can be present on one or more bases or be universally present on each base (i.e. all cytosines are present as 5' methylcytosine). Additionally, the ON chelate complexes can comprise ONs which contain multiple modifications such as each linkage phosphorothioated, each ribose 2' modified and each base modified. ON modifications compatible with ON chelate complex formation are further defined above. Moreover, the chelation of the metal cations is not dependent on the sequence of nucleotides present but instead relies on the physiochemical features common to all ONs.

While the formation of ON chelate complexes can be achieved with any divalent metal cation, ON chelate complexes intended for use as medications should preferably contain only calcium and or magnesium but could also contain iron, manganese, copper or zinc in trace amounts and should not include cobalt, barium, nickel, cadmium, mercury, lead or any other divalent metal not listed herein.

As described in U.S. 2014/0065192, the removal of HBsAg from the blood of infected patients by phosphorothioated NAPs results in a partial restoration of the immune response which in turn removes HBV e-antigen (HBeAg) from the blood and results in substantial reduction of levels of virus in the blood during treatment but these antiviral effects are not maintained in most patients after treatment is stopped. While this partial restoration of the immune response (in the absence of HBsAg and other viral antigens) can lead to the establishment of durable immunological control of HBV infection after treatment is stopped in a small proportion of patients, it is desirable to establish durable immunological control of infection in an even larger proportion of patients. An improvement in the proportion of patients that achieve durable immunological control after treatment can be achieved by using phosphorothioated NAPs in combination with other antiviral agents to improve the speed and potency of antiviral response to treatment. It would be desirable to avoid the use of immunotherapies as such as interferon-based treatment or other immunotherapies as these are typically associated with side effects which make therapy more difficult to tolerate for patients.

The term "removal of HBsAg from the blood" as used herein means any statistically significant reduction of the concentration HBsAg in the blood relative to pre-treatment HBsAg blood concentrations as measured by the Abbott Architect™ quantitative HBsAg assay or other clinically accepted quantitative measure of serum HBsAg.

Exemplary effective dosing regimens for phosphorothioated NAPs follow those typically used for other phosphorothioated ONs (such as antisense oligonucleotides) as described in U.S. 2014/0065102; the routine use of weekly parenteral administration of 100-500 mg of compound is well established in the art to result in the achievement of therapeutically active levels of these compounds in the liver as described for the NAPs in example I below and for a phosphorothioated antisense ON causing the degradation of a liver specific mRNA (for apolipoprotein B100) as described in Akdim et al. (2010, Journal of the American College of Cardiology, 55: 1611-1618).

Therefore, according to the disclosures presented herein, it is useful to treat a subject with HBV infection or HBV/HDV co-infection with a pharmaceutically acceptable phosphorothioated NAP formulation combined with a pharmaceutically acceptable nucleoside/nucleotide HBV polymerase inhibitor.

It is also useful to administer both pharmaceutically acceptable agents in the same pharmaceutical composition or to administer both pharmaceutically acceptable agents in separate pharmaceutical compositions at the same time or at different times.

It is useful to administer the pharmaceutically acceptable agents by the same or different routes of administration.

In order to provide the best possible antiviral response in a subject, it may be necessary to use more than one HBV polymerase inhibitors to maximally block the HBV polymerase and thus have maximal greater effect on blocking the replenishment of cccDNA. Thus one or more HBV polymerase inhibitors can be selected from the following nucleoside analogs:

lamivudine;
adefovir dipivoxil;
entecavir;
telbivudine;
tenofovir disoproxil fumarate;
entricitabine;
clevudine;
besifovir;
tenofovir alafenamide fumarate;
AGX-1009;
elvucitabine;
lagociclovir valactate;
pradefovir mesylate;
valtorcitabine; and
any nucleoside/nucleotide analog which inhibits the HBV polymerase.

The compositions described herein may be administered by any suitable means, for example, orally, such as in the form of tablets, capsules, granules or powders; sublingually; buccally; parenterally, such as by subcutaneous, intravenous, injection or infusion techniques (e.g., as sterile injectable aqueous or non-aqueous solutions or suspensions); by inhalation; topically, such as in the form of a cream or ointment; or rectally such as in the form of suppositories or enema; in dosage unit formulations containing non-toxic, pharmaceutically acceptable vehicles or diluents. The present compositions may, for example, be administered in a form suitable for immediate release or extended release. Immediate release or extended release may be achieved by the use of suitable pharmaceutical compositions, or, particularly in the case of extended release, by the use of devices such as subcutaneous implants or osmotic pumps. Thus, the above compositions may be adapted for administration by any one of the following routes: oral ingestion, inhalation, subcutaneous injection, intravenous injection or infusion, or topically.

The present disclosure will be more readily understood by referring to the following example.

EXAMPLE I

Effect of Combination NAP/ETV Therapy on Serum HBsAg

A pharmaceutically acceptable formulation of the NAP REP 2055 (SEQ ID NO: 2) was administered to a patient with chronic HBV infection by once weekly IV infusion of 400 mg. The serum HBsAg response in this patient was monitored real-time each week using a qualified, on-site qualitative ELISA. This ELISA method is very sensitive to low levels of HBsAg but cannot accurately quantify any significant HBsAg concentration in the blood. Although no detectable reduction in serum HBsAg was observed using this HBsAg assay during REP 2055 monotherapy (FIG. 1, squares), this patient experienced a very mild (~1 log) drop in serum virema (serum HBV DNA), indicating that some sort of antiviral response had occurred. Therefore, after 29 weeks of REP 2055 monotherapy, this patient received HBV polymerase inhibition therapy in addition to the existing REP 2055 therapy which consisted of 0.5 mg of entecavir taken orally every day.

Figure 1:
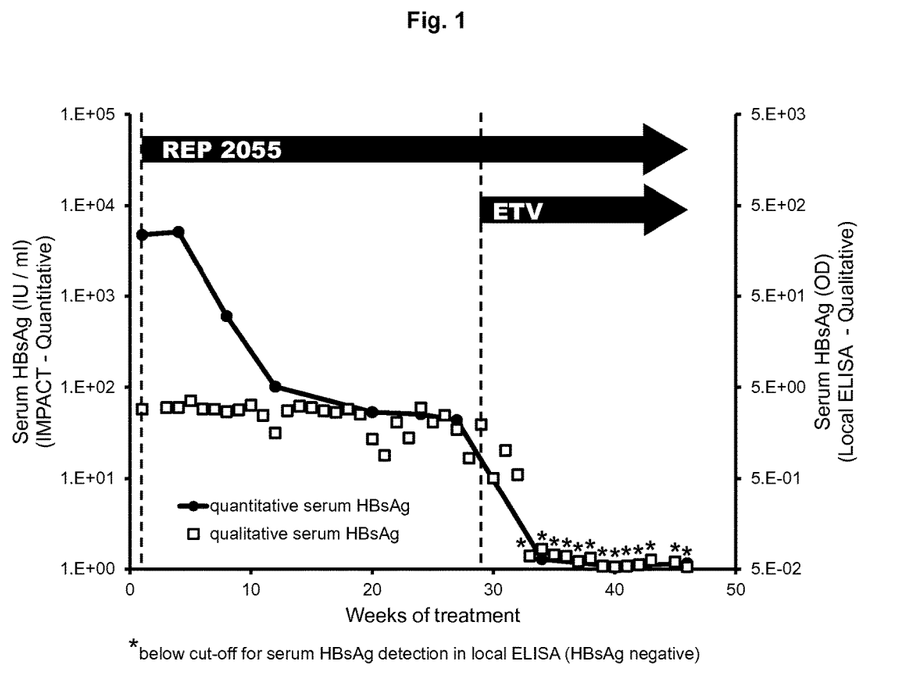
FIG. 1 illustrates the synergistic effect of combination therapy with the NAP REP 2055 (SEQ ID NO: 2) and entecavir (ETV) on the reduction of serum levels of HBsAg.

Immediate reductions in serum HBsAg were detected by the qualitative assay within two weeks of starting combination REP 2055/ETV therapy and serum HBsAg became undetectable in the qualitative ELISA within 4 weeks after starting combination treatment (FIG. 1, squares). This synergistic control of serum HBsAg with combined REP 2055/ETV treatment was maintained over many weeks of treatment.

To confirm the synergistic activity of combination REP 2055/ETV therapy on suppression of HBsAg, serum samples from this patient were re-analyzed using the IMPACT platform to accurately quantitate serum HBsAg levels as described in de Neit et al. (2014, Antiviral Ther., 19: 259-267). This quantitative analysis revealed an initial ~2 log reduction of serum HBsAg occurred with REP 2055 monotherapy (FIG. 1 circles), which was not detectable by the qualitative ELISA and which was likely the cause of the observed ~1 log drop in viremia on REP 2055 monotherapy described above. Importantly, serum HBsAg reduction in this patient reached a plateau where significant serum HBsAg was stably present starting from 10 weeks of REP 2055 treatment until the start of combination REP 2055/ETV therapy at 29 weeks of treatment. With the onset of combination REP 2055/ETV treatment, the quantitative analysis of serum HBsAg demonstrated an almost identical and rapid reduction in serum HBsAg as observed with the onsite qualitative test, with these additional reductions exceeding 1.5 logs which were also accomplished within 4 weeks after the start of combination REP 2055/ETV treatment.

The persistence of low levels of serum HBsAg in the presence of REP 2055 monotherapy is an indication that cccDNA was still present in the liver of this patient which was transcriptionally active. The very rapid additional clearance of serum HBsAg with the addition of ETV to existing REP 2055 therapy is an indication that a synergistic effect on cccDNA transcriptional control and or elimination had occurred. Importantly, the development of this additional control of cccDNA occurred much more rapidly than observed with HBV polymerase inhibitors used in monotherapy, requiring only 4 weeks to achieve. Therefore, these observations are a demonstration of the novel, synergistic antiviral effect of serum HBsAg reduction (in this case achieved using the NAP REP 2055) when combined with an HBV polymerase inhibitor (in this case entecavir).

EXAMPLE II

Antiviral Effects of Various NAPs in DHBV Infected Pekin Ducks

Various NAPs comprising different nucleic acid modifications were tested in DHBV infected Pekin ducks to establish their antiviral activity. These NAPs are REP 2055 (SEQ ID NO: 2), REP 2139 (SEQ ID NO: 10), REP 2163 (SEQ ID NO: 11) and REP 2165 (SEQ ID NO: 13). Table 2 provides a chemical description of these NAPs.

TABLE 2

Description of NAPs used in Example II

Figure 2A:
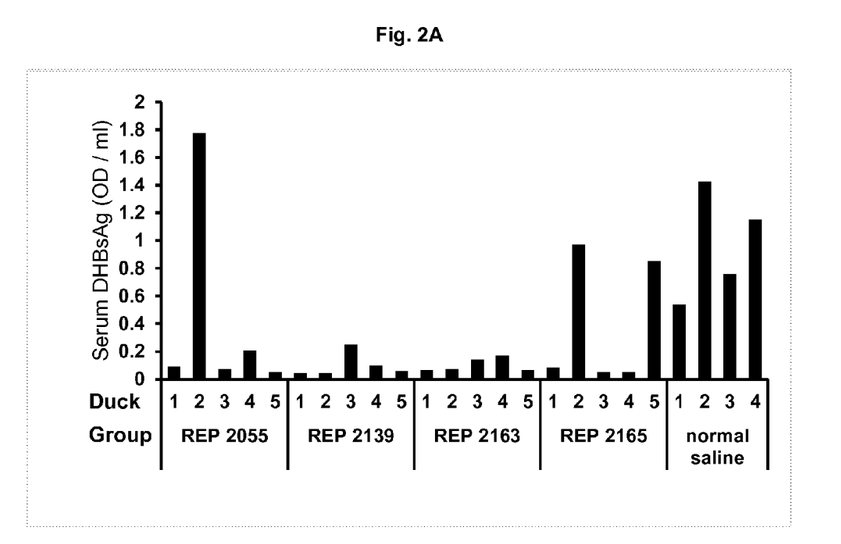
FIG. 2A illustrates the antiviral activity of NAPs administered to infected Pekin ducks as calcium chelate complexes with DHBV measured by monitoring serum DHBsAg at the end of treatment by ELISA
Figure 2B:
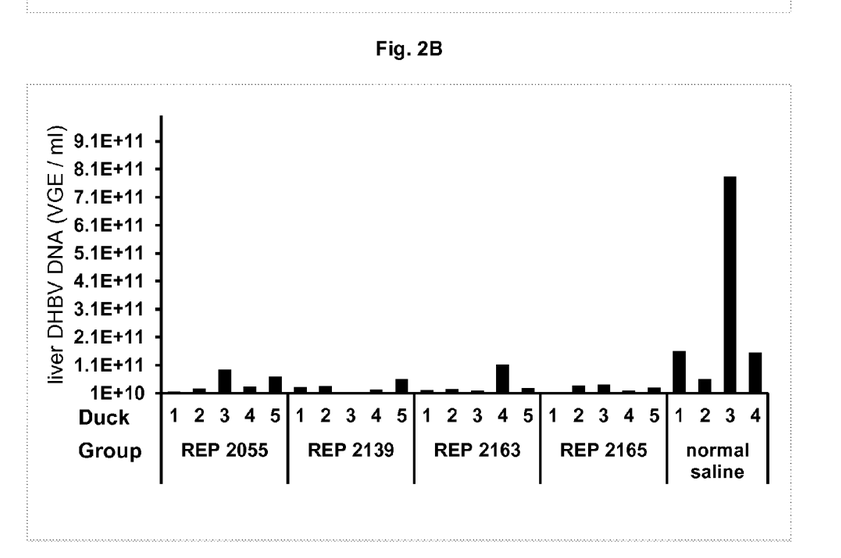
FIG. 2B illustrates the antiviral activity of NAPs administered to infected Pekin ducks as calcium chelate complexes with DHBV assessed by monitoring liver DHBV DNA at the end of treatment by quantitative PCR.

| NAP | Sequence | Oligonucleotide modifications present |
|---|---|---|
| REP 2055 (SEQ ID NO: 2) | $(dAdC)_{20}$ | Each linkage is phosphorothioated |
| REP 2139 (SEQ ID NO: 10) | $(A, 5'MeC)_{20}$ | Each linkage is phosphorothioated Every ribose is 2'O methylated |
| REP 2163 (SEQ ID NO: 11) | $(A, 5'MedC)_{20}$ | Each linkage is phosphorothioated Only the riboses in adenosine are 2'O methylated |
| REP 2165 (SEQ ID NO: 13) | $(A, 5'MeC)_{20}$ | Each linkage is phosphorothioated Every ribose is 2'O methylated except adenosines at positions 11, 21 and 31 where riboses are 2'OH. | dA = deoxyriboadenosine
dC = deoxyribocytidine
A = riboadenosine
5'MeC = ribo-5'methylcytidine
5'MedC = deoxyribo = 5'methylcytidine Three-day-old Pekin ducklings were infected with $2 \times 10^{11}$ viral genome equivalents (VGE)/ml of DHBV. NAP treatment was started 11 days later after infection had become established. NAPs were administered via intraperitoneal injection with 10 mg/kg of NAPs (formulated as calcium chelate complexes) 3 times/week for three weeks followed by analysis of antiviral effect at the end of treatment. A control group was treated with normal saline via the same route of administration and with the same dosing regimen. Antiviral activity was assessed by monitoring serum DHBsAg by ELISA (FIG. 2A) and liver DHBV DNA by quantitative PCR (FIG. 2B).

All NAPs resulted in reductions in serum DHBsAg and liver DHBV DNA, demonstrating that different NAPs containing diverse oligonucleotide modifications will have comparable antiviral effect. This in turn indicates that the synergistic antiviral activity observed with the use of a specific NAP and one or more nucleoside analog based HBV polymerase inhibitors (as observed with REP 2055 and entecavir in Example I above) will occur with any other phosphorothioated NAP and also with any said phosphorothioated NAP formulated as a chelate complex (as described in U.S. Pat. Nos. 8,513,211 and 8,716,259).

EXAMPLE III

Antiviral Effects of NAPs in Combination with TDF and ETV in DHBV Infected Pekin Ducks The antiviral effect of combined treatment with the calcium chelate complex of REP 2139 (REP 2139-Ca) and TDF or REP 2139-Ca and TDF and ETV in DHBV infected Pekin ducks was examined by assessing changes in the levels of serum and liver DHBV DNA during and after treatment by quantitative PCR. Infection of ducks was carried out as described in Example II except that treatment was started one month after infection. Treatment regimens were as follows:

1) Normal saline given by IP injection 3 times per week for 4 weeks
2) TDF, given 15 mg/day by oral gavage for 28 days
3) REP 2139-Ca, given 10 mg/kg by IP injection, 3 times per week for 4 weeks.
4) REP 2139-Ca and TDF (as dosed above)
5) REP 2139-Ca and TDF (as dosed above) and ETV given 1 mg/day by oral gavage for 28 days.

Serum DHBV DNA was assessed pre-treatment (time point A), at day 14 of treatment (time point B), at the end of treatment (time point C), and one and two months after treatment was stopped (follow-up, time point D and E).

Figure 3A:
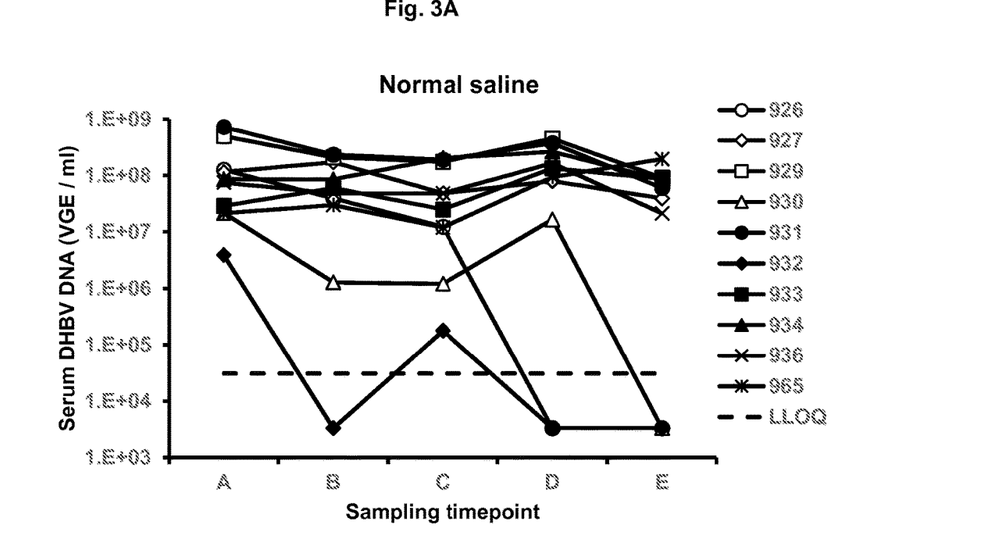
FIG. 3A illustrates the levels of DHBV DNA in the serum of ducks treated 28 days with normal saline at: A) pre-treatment, B) when treatment is half completed, C) end of treatment, D) one month after treatment and E) two months after treatment. The lower limit of quantification (LLOQ) is $3.1 \times 10^4$ VGE/ml. Values<LLOQ were set at $3 \times 10^3$ VGE/ml. VGE=viral genome equivalents.
Figure 3B:
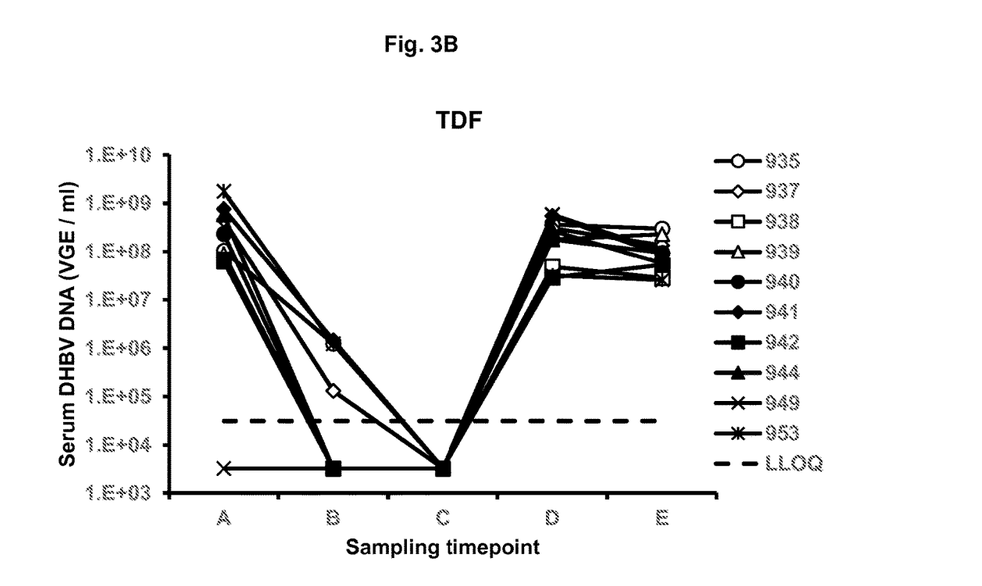
FIG. 3B illustrates the levels of DHBV DNA in the serum of ducks treated for 28 days with tenofovir disoproxil fumarate (TDF) at: A) pre-treatment, B) when treatment is half completed, C) end of treatment, D) one month after treatment and E) two months after treatment. The lower limit of quantification (LLOQ) is $3.1 \times 10^4$ VGE/ml. Values<LLOQ were set at $3 \times 10^3$ VGE/ml. VGE=viral genome equivalents.
Figure 3C:
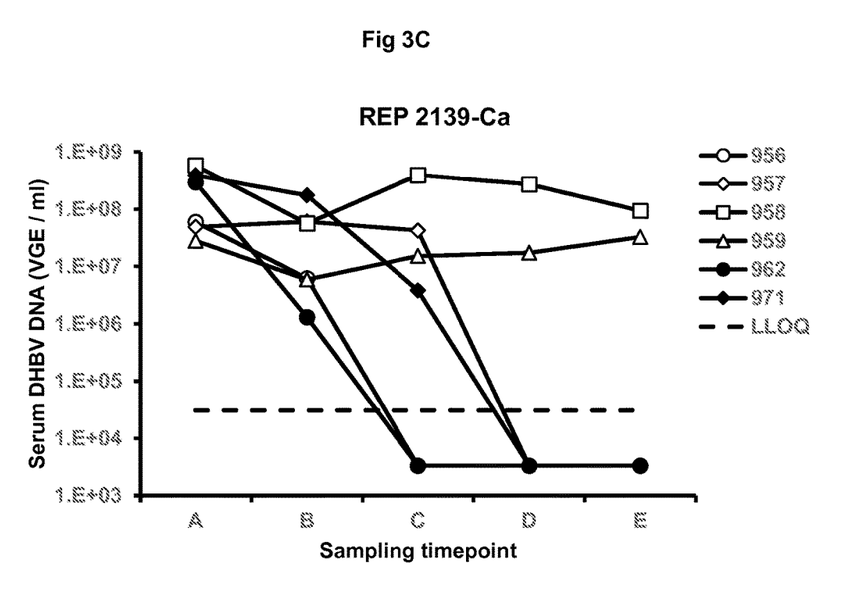
FIG. 3C illustrates the levels of DHBV DNA in the serum of ducks treated for 28 days with REP 2139-Ca at: A) pre-treatment, B) when treatment is half completed, C) end of treatment, D) one month after treatment and E) two months after treatment. The lower limit of quantification (LLOQ) is $3.1 \times 10^4$ VGE/ml. Values<LLOQ were set at $3 \times 10^3$ VGE/ml. VGE=viral genome equivalents.
Figure 3D:
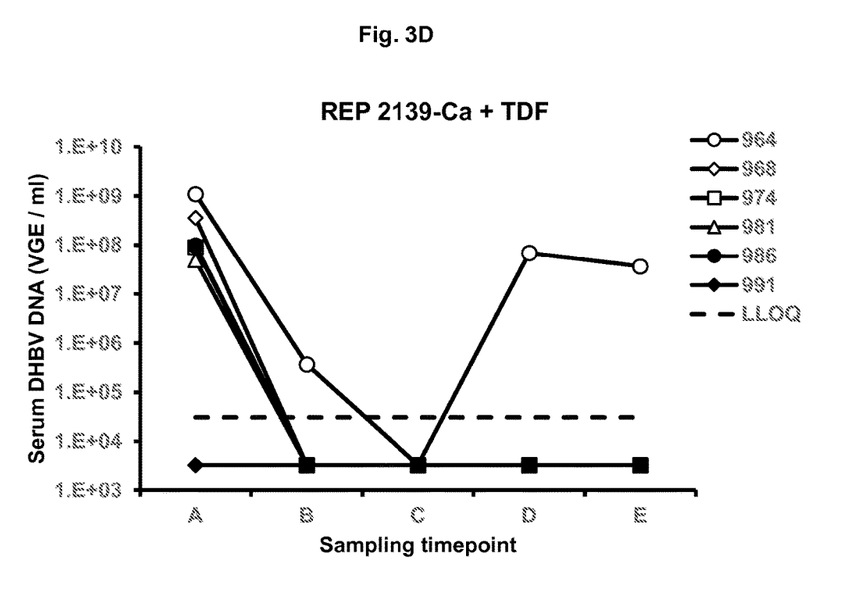
FIG. 3D illustrates the levels of DHBV DNA in the serum of ducks treated for 28 days with REP 2139-Ca and TDF at: A) pre-treatment, B) when treatment is half completed, C) end of treatment, D) one month after treatment and E) two months after treatment. The lower limit of quantification (LLOQ) is $3.1 \times 10^4$ VGE/ml. Values<LLOQ were set at $3 \times 10^3$ VGE/ml. VGE=viral genome equivalents.
Figure 3E:
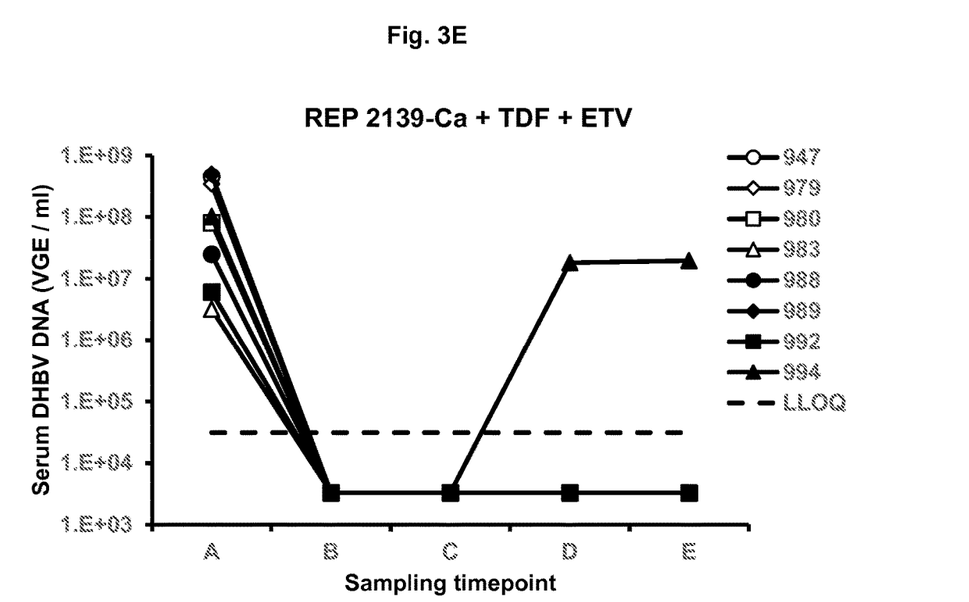
FIG. 3E illustrates the levels of DHBV DNA in the serum of ducks treated for 28 days with REP 2139-Ca, TDF and entecavir (ETV) at: A) pre-treatment, B) when treatment is half completed, C) end of treatment, D) one month after treatment and E) two months after treatment. The lower limit of quantification (LLOQ) is $3.1 \times 10^4$ VGE/ml. Values<LLOQ were set at $3 \times 10^3$ VGE/ml. VGE=viral genome equivalents.

In the normal saline treated group, no control of DHBV DNA was observed during treatment, although DHBV DNA became spontaneously controlled in 3 ducks in this group during the follow-up (FIG. 3A). In the TDF-treated group serum DHBV DNA was reduced in all ducks but control was not achieved in all ducks until the end of treatment. DHBV DNA rebounded in all ducks in this group during follow-up (FIG. 3B). In the REP 2139-Ca treated group, no change in DHBV DNA was observed in two ducks throughout the study, DHBV DNA was controlled at the end of treatment in only two ducks and became spontaneously controlled in two additional ducks during the follow-up (FIG. 3C). When REP 2139-Ca was combined with TDF control of DHBV DNA occurred in all but one duck halfway through treatment and was generally more rapid than the control achieved in the groups treated with either REP 2139-Ca or TDF alone. When REP 2139-Ca was combined with TDF and ETV, DHBV was controlled in all ducks halfway through the treatment (FIG. 3E). The proportion of ducks that maintained control of serum DHBV DNA during follow-up was greater with combined REP 2139-Ca and TDF (or TDF and ETV) than with TDF or REP 2139-Ca alone (FIGS. 3D and E).

These observations teach that the on-treatment antiviral response in HBV infection can be improved synergistically by combining REP 2139-Ca and TDF or TDF and ETV and can lead to improved sustained virologic response off-treatment compared to that achieved with REP 2139-Ca or TDF alone. The synergistic activity seen in the above example can be reliability expected to occur with any NAP active against HBV as described herein and with any nucleotide/nucleoside analog based HBV polymerase inhibitor as described herein. Further, NAPs used in combination with more than one nucleoside/nucleotide HBV polymerase inhibitor can also be used with similarly productive synergistic antiviral effect.

The synergistic effects of combined NAP/TDF/ETV treatment led to the improved speed of antiviral response, demonstrating the potential for shorter treatment regimens capable of achieving sustained virologic response off-treatment. This potential could also be realized with any combination of NAP and nucleotide/nucleoside analog HBV polymerase inhibitor treatment as described herein.

Therefore, these observations teach that any pharmaceutically acceptable phosphorothioated NAP formulation which reduces or removes HBsAg from the blood (as described in U.S. 2014/0065102 and U.S. Pat. Nos. 8,008,269, 8,008,270 and 8,067,385) could be combined with any nucleoside/nucleotide HBV polymerase inhibitor as listed above and be expected to achieve a synergistic effect on the speed with which control of serum viremia can be achieved and or the transcriptional inactivation and or elimination of HBV cccDNA. The synergistic effects observed also teach that lower doses of said pharmaceutically acceptable agents could be combined and still achieve a synergistic activity with a useful antiviral effect.

Given the synergistic antiviral effects observed above with one phosphorothioated NAP used in combination with one nucleoside/nucleotide HBV polymerase inhibitor, a superior synergistic effect could also be achieved with one or more phosphorothioated NAPs used in combination with one or more nucleoside/nucleotide HBV polymerase inhibitors as described above.

The above description is meant to be exemplary only, and one skilled in the art will recognize that changes may be made to the embodiments described without departing from the scope of the invention as defined by the appended claims. Still other modifications which fall within the scope of the present invention, as defined in the appended claims, will be apparent to those skilled in the art, in light of a review of this disclosure, without departing from the scope of the invention as defined by the appended claims.

What is claimed is:

1. A method for treating HBV infection or HBV/HDV co-infection in a subject comprising administering a first pharmaceutically acceptable agent which comprises a chelate complex of at least one phosphorothioated nucleic acid polymer and a second pharmaceutically acceptable agent which comprises at least one nucleoside/nucleotide analog HBV polymerase inhibitor.

2. The method of claim 1, wherein the nucleic acid polymer further comprises at least one 2' ribose modification.

3. The method of claim 1, wherein the nucleic acid polymer further comprises all riboses having a 2' modification.

4. The method of claim 1, wherein the nucleic acid polymer further comprises at least one 2' O methyl ribose modification.

5. The method of claim 1, wherein the nucleic acid polymer further comprises all riboses having the 2' O methyl modification.

6. The method of claim 1, wherein the nucleic acid polymer further comprises at least one 5' methylcytosine.

7. The method of claim 1, wherein the nucleic acid polymer further comprises all cytosines present as 5' methylcytosine.

8. The method of claim 1, wherein the nucleic acid polymer further comprises at least one 2' O methyl ribose modification and at least one 5' methylcytosine.

9. The method of claim 1, wherein the nucleic acid polymer further comprises all riboses having the 2' O methyl modification and all cytosines present as 5' methylcytosine.

10. The method of claim 1, wherein the chelate complex is a calcium chelate complex.

11. The method of claim 1, wherein the chelate complex is a magnesium chelate complex.

12. The method of claim 1, wherein the chelate complex is a calcium/magnesium chelate complex.

13. The method of claim 1, wherein said first and second pharmaceutically acceptable agents are formulated within the same pharmaceutical composition.

14. The method of claim 1, where said first and second pharmaceutically acceptable agents are formulated within separate pharmaceutical compositions.

15. The method of claim 1, wherein said first and second pharmaceutically acceptable agents are administered simultaneously.

16. The method of claim 1, wherein said first and second pharmaceutically acceptable agents are administered by a different route.

17. The method of claim 1, wherein said first and second pharmaceutically acceptable agents are administered using one or more of the following: oral ingestion, aerosol inhalation, subcutaneous injection, intravenous injection and intravenous infusion.

18. A method of treating HBV infection or HBV/HDV co-infection in a subject comprising administering a first pharmaceutically acceptable agent which comprises a chelate complex of one or more nucleic acid polymers selected from the following:
SEQ ID NO: 2;
SEQ ID NO: 10;
SEQ ID NO 13;
SEQ ID NOs: 1, 3-9, 11, 12 and 14-20;
a phosphorothioated oligonucleotide from 20-120 nucleotides in length comprising repeats of the sequence AC;
a phosphorothioated oligonucleotide from 20-120 nucleotides in length comprising repeats of the sequence CA;
a phosphorothioated oligonucleotide from 20-120 nucleotides in length comprising repeats of the sequence TG and
a phosphorothioated oligonucleotide from 20-120 nucleotides in length comprising repeats of the sequence GT;
and a second pharmaceutically acceptable agent which comprises one or more of the following:
lamivudine;
adefovir dipivoxil;
entecavir;
telbivudine;
tenofovir disoproxil fumarate;
entricitabine;
clevudine;
besifovir;
tenofovir alafenamide fumarate;
AGX-1009;
elvucitabine;
lagociclovir valactate;
pradefovir mesylate;
valtorcitabine; and
any nucleoside/nucleotide analog which inhibits the HBV polymerase.

* * * * *